(12) United States Patent
Burstein

(10) Patent No.: US 11,135,211 B2
(45) Date of Patent: Oct. 5, 2021

(54) PIMAVANSERIN FOR TREATING IMPULSE CONTROL DISORDER

(71) Applicant: ACADIA Pharmaceuticals Inc., San Diego, CA (US)

(72) Inventor: Ethan S. Burstein, San Diego, CA (US)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 16/607,234

(22) PCT Filed: Apr. 27, 2018

(86) PCT No.: PCT/US2018/029831
§ 371 (c)(1),
(2) Date: Oct. 22, 2019

(87) PCT Pub. No.: WO2018/200977
PCT Pub. Date: Nov. 1, 2018

(65) Prior Publication Data
US 2020/0061045 A1 Feb. 27, 2020

Related U.S. Application Data

(60) Provisional application No. 62/491,820, filed on Apr. 28, 2017.

(51) Int. Cl.
*A61K 31/4468* (2006.01)
*A61P 25/18* (2006.01)
*A61K 31/197* (2006.01)

(52) U.S. Cl.
CPC ........ *A61K 31/4468* (2013.01); *A61K 31/197* (2013.01); *A61P 25/18* (2018.01)

(58) Field of Classification Search
CPC .................................................. A61K 31/4468
See application file for complete search history.

(56) References Cited

U.S. PATENT DOCUMENTS

| | | |
|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,853,394 A | 8/1989 | King |
| 5,025,013 A | 6/1991 | Barreau |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda |
| 5,707,798 A | 1/1998 | Brann |
| 5,795,894 A | 8/1998 | Shue |
| 5,837,730 A | 11/1998 | Javitt |
| 5,869,488 A | 2/1999 | Shue |
| 5,877,173 A | 3/1999 | Olney et al. |
| 5,912,132 A | 6/1999 | Brann |
| 5,955,281 A | 9/1999 | Brann |
| 6,107,324 A | 8/2000 | Behan |
| 6,140,509 A | 10/2000 | Behan |
| 6,150,393 A | 11/2000 | Behan |
| 6,358,698 B1 | 3/2002 | Weiner et al. |
| 6,451,343 B1 | 9/2002 | Glinecke et al. |
| 6,479,480 B1 | 11/2002 | Moyes |
| 6,486,153 B1 | 11/2002 | Castro Pineiro |
| 6,670,137 B2 | 12/2003 | VanMechelen et al. |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,087,593 B2 | 8/2006 | Kelly et al. |
| 7,115,634 B2 | 10/2006 | Thurieau et al. |
| 7,217,719 B2 | 5/2007 | Schlienger |
| 7,253,186 B2 | 8/2007 | Andersson et al. |
| 7,351,707 B2 | 4/2008 | Schlienger |
| 7,393,861 B2 | 7/2008 | Thurieau et al. |
| 7,476,682 B2 | 1/2009 | Andersson et al. |
| 7,538,222 B2 | 5/2009 | Andersson et al. |
| 7,601,740 B2 | 10/2009 | Weiner et al. |
| 7,659,285 B2 | 2/2010 | Weiner et al. |
| 7,713,995 B2 | 5/2010 | Weiner et al. |
| 7,732,462 B2 | 6/2010 | Weiner et al. |
| 7,732,615 B2 | 6/2010 | Thygesen et al. |

(Continued)

FOREIGN PATENT DOCUMENTS

| | | |
|---|---|---|
| CA | 984843 A | 3/1976 |
| CN | 104844502 A | 8/2015 |

(Continued)

OTHER PUBLICATIONS

Cunningham et al., 2014, "Serotonin at the nexus of impulsivity and cue reactivity in cocaine addiction," Neuropharmacology, 76 Pt B:460-478.
Prescribing Information for Nuplazid™ (pimavanserin) tablets, for oral use, Revised: Apr. 2016 (14 pages).
Vanover et al., 2006, "Pharmacological and behavioral profile of N-(4-fluorophenylmethyl)-N-(1-methylpiperidin-4-yl)-N'-(4-(2-methylpropyloxy)phenylmethyl) carbamide (2R,3R)-dihydroxybutanedioate (2:1) (ACP-103), a novel 5-hydroxytryptamine(2A) receptor inverse agonist," J Pharmacol Exp Ther., 317(2):910-918.
Vanover et al., 2007, "Pharmacokinetics, tolerability, and safety of ACP-103 following single or multiple oral dose administration in healthy volunteers," J Clin Pharmacol., 47(6):704-714.
Weintraub et al., 2006, "Association of dopamine agonist use with impulse control disorders in Parkinson disease," Arch Neurol., 63(7):969-973.

(Continued)

*Primary Examiner* — Golam M Shameem
(74) *Attorney, Agent, or Firm* — Goodwin Procter LLP

(57) ABSTRACT

A method for treating a impulse control disorder in a patient comprising administering to the patient an effective amount of pimavanserin or a pharmaceutical acceptable salt thereof.

20 Claims, No Drawings

(56) References Cited

U.S. PATENT DOCUMENTS

| | | |
|---|---|---|
| 7,790,899 B2 | 9/2010 | Tolf et al. |
| 7,816,383 B1 | 10/2010 | Bradford et al. |
| 7,820,695 B2 | 10/2010 | Weiner et al. |
| 7,858,789 B2 | 12/2010 | Thurieau et al. |
| 7,863,296 B2 | 1/2011 | Weiner et al. |
| 7,868,176 B2 | 1/2011 | Thygesen et al. |
| 7,875,632 B2 * | 1/2011 | Weiner .................. A61P 25/00 514/317 |
| 7,923,564 B2 | 4/2011 | Thygesen et al. |
| 7,994,193 B2 | 8/2011 | Weiner et al. |
| 8,008,323 B2 | 8/2011 | Weiner et al. |
| 8,110,574 B2 | 2/2012 | Thurieau et al. |
| 8,227,487 B2 | 7/2012 | Weiner et al. |
| 8,236,960 B2 | 8/2012 | Thygesen et al. |
| 8,377,959 B2 | 2/2013 | Weiner et al. |
| 8,618,130 B2 | 12/2013 | Weiner et al. |
| 8,921,393 B2 | 12/2014 | Weiner et al. |
| 9,050,343 B2 | 6/2015 | Peters et al. |
| 9,211,289 B2 | 12/2015 | Weiner et al. |
| 9,296,694 B2 | 3/2016 | Andersson et al. |
| 9,446,037 B2 | 9/2016 | Mills et al. |
| 9,486,453 B2 | 11/2016 | Javitt |
| 9,566,271 B2 | 2/2017 | Weiner et al. |
| 9,757,366 B2 | 9/2017 | Mills et al. |
| 9,765,053 B2 | 9/2017 | Andersson et al. |
| 10,028,944 B2 | 7/2018 | Weiner et al. |
| 10,449,185 B2 | 10/2019 | Tejwani et al. |
| 10,517,860 B2 | 12/2019 | Parkinson |
| 10,525,046 B2 | 1/2020 | Weiner et al. |
| 10,597,363 B2 | 3/2020 | Carlos et al. |
| 10,646,480 B2 | 5/2020 | Tejwani et al. |
| 10,849,891 B2 | 12/2020 | Tejwani et al. |
| 10,953,000 B2 | 3/2021 | Parkinson |
| 10,981,870 B2 | 4/2021 | Carlos et al. |
| 10,981,871 B2 | 4/2021 | Carlos et al. |
| 2002/0156068 A1 | 10/2002 | Behan |
| 2002/0165225 A1 | 11/2002 | Kankan et al. |
| 2004/0006081 A1 | 1/2004 | Burrows |
| 2004/0106600 A1 | 6/2004 | Andersson et al. |
| 2004/0213816 A1 | 10/2004 | Weiner et al. |
| 2004/0229908 A1 | 11/2004 | Nelson |
| 2005/0014757 A1 | 1/2005 | Andersson et al. |
| 2005/0148018 A1 | 7/2005 | Weiner et al. |
| 2005/0244862 A1 | 11/2005 | Brann |
| 2005/0256108 A1 | 11/2005 | Schlienger |
| 2005/0261278 A1 | 11/2005 | Weiner et al. |
| 2005/0261340 A1 | 11/2005 | Weiner et al. |
| 2005/0288328 A1 | 12/2005 | Weiner et al. |
| 2006/0094758 A1 | 5/2006 | Andersson et al. |
| 2006/0106063 A1 | 5/2006 | Thhygesen et al. |
| 2006/0111399 A1 | 5/2006 | Thhygesen et al. |
| 2006/0194778 A1 | 8/2006 | Andersson et al. |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |
| 2006/0204486 A1 | 9/2006 | Pyke et al. |
| 2006/0205710 A1 | 9/2006 | Schlienger |
| 2006/0205722 A1 | 9/2006 | Andersson et al. |
| 2006/0205780 A1 | 9/2006 | Thygesen et al. |
| 2006/0205781 A1 | 9/2006 | Thygesen et al. |
| 2006/0264465 A1 | 11/2006 | Weiner et al. |
| 2006/0264466 A1 | 11/2006 | Weiner et al. |
| 2006/0286610 A1 | 12/2006 | Brann |
| 2006/0292606 A1 | 12/2006 | Brann |
| 2007/0260064 A1 | 11/2007 | Tolf et al. |
| 2007/0264330 A1 | 11/2007 | Ragnar-Tolf et al. |
| 2008/0051429 A1 | 2/2008 | Van Kammen et al. |
| 2008/0280886 A1 | 11/2008 | Gant et al. |
| 2009/0053329 A1 | 2/2009 | Peters et al. |
| 2009/0082342 A1 | 3/2009 | Uldam et al. |
| 2009/0082388 A1 | 3/2009 | Hacksell |
| 2009/0186921 A1 | 7/2009 | Andersson et al. |
| 2014/0018348 A1 | 1/2014 | Javitt |
| 2014/0162942 A1 | 6/2014 | Ghosal et al. |
| 2014/0221395 A1 | 8/2014 | Dhanoa |
| 2014/0329903 A1 | 11/2014 | Burstein et al. |
| 2014/0349976 A1 | 11/2014 | Hacksell et al. |
| 2015/0231126 A1 | 8/2015 | Peters |
| 2015/0313888 A1 | 11/2015 | Mills et al. |
| 2016/0237036 A1 | 8/2016 | Andersson et al. |
| 2018/0037549 A1 | 2/2018 | Biljan |
| 2019/0030015 A1 | 1/2019 | Weiner et al. |
| 2019/0047955 A1 | 2/2019 | Carlos et al. |
| 2019/0117636 A1 | 4/2019 | Burstein |
| 2019/0216791 A1 | 7/2019 | Tejwani et al. |
| 2019/0231767 A1 | 8/2019 | Parkinson |
| 2019/0240211 A1 | 8/2019 | Parkinson |
| 2020/0009122 A1 | 1/2020 | Tejwani et al. |
| 2020/0078346 A1 | 3/2020 | Parkinson |
| 2020/0165202 A1 | 5/2020 | Carlos et al. |
| 2020/0181087 A1 | 6/2020 | Carlos et al. |
| 2020/0222381 A1 | 7/2020 | Tejwani et al. |
| 2020/0237739 A1 | 7/2020 | Coate et al. |
| 2020/0323836 A1 | 10/2020 | Weiner et al. |
| 2021/0077479 A1 | 3/2021 | Tejwani et al. |

FOREIGN PATENT DOCUMENTS

| | | |
|---|---|---|
| CN | 104961672 A | 10/2015 |
| CN | 105111135 A | 12/2015 |
| CN | 105153016 A | 12/2015 |
| CN | 105418460 A | 3/2016 |
| CN | 105481757 A | 4/2016 |
| CN | 105820110 A | 8/2016 |
| CN | 106543072 A | 3/2017 |
| EP | 0005318 B1 | 11/1979 |
| EP | 0061333 B1 | 9/1982 |
| EP | 0260070 B1 | 3/1988 |
| EP | 0379441 A1 | 7/1990 |
| EP | 0548015 B1 | 6/1993 |
| EP | 0625507 B1 | 11/1994 |
| EP | 1576985 A1 | 9/2005 |
| HU | 157325 | 3/1998 |
| JP | 51052176 | 5/1976 |
| JP | 52085174 A | 7/1977 |
| WO | WO-9427967 A1 | 12/1994 |
| WO | WO-9708166 A1 | 3/1997 |
| WO | WO-9711940 A1 | 4/1997 |
| WO | WO-9738665 A2 | 10/1997 |
| WO | WO-9738984 A1 | 10/1997 |
| WO | WO-9811128 A1 | 3/1998 |
| WO | WO-9817646 A1 | 4/1998 |
| WO | WO-98/44921 A1 | 10/1998 |
| WO | WO-98/50534 A1 | 11/1998 |
| WO | WO-9952927 A1 | 10/1999 |
| WO | WO-0023076 A1 | 4/2000 |
| WO | WO-0056335 A1 | 9/2000 |
| WO | WO-0059497 A1 | 10/2000 |
| WO | WO-0069810 A1 | 11/2000 |
| WO | WO-0144191 A1 | 6/2001 |
| WO | WO-0166521 A1 | 9/2001 |
| WO | WO-0187839 A1 | 11/2001 |
| WO | WO-2001089498 A2 | 11/2001 |
| WO | WO-0224649 A1 | 3/2002 |
| WO | WO-2002038142 A2 | 5/2002 |
| WO | WO-02076464 A1 | 10/2002 |
| WO | WO-02079186 A2 | 10/2002 |
| WO | WO-03057698 A2 | 7/2003 |
| WO | WO-03062206 A2 | 7/2003 |
| WO | WO-03070246 A1 | 8/2003 |
| WO | WO-03086400 A1 | 10/2003 |
| WO | WO-04000808 A2 | 12/2003 |
| WO | WO-04039322 A2 | 5/2004 |
| WO | WO-04064753 A2 | 8/2004 |
| WO | WO-2004064738 A2 | 8/2004 |
| WO | WO-05053796 A1 | 6/2005 |
| WO | WO-05063254 A2 | 7/2005 |
| WO | WO-05112927 A1 | 12/2005 |
| WO | 2006036874 A1 | 4/2006 |
| WO | 2006037043 A1 | 4/2006 |
| WO | WO-06104826 A2 | 10/2006 |
| WO | WO-2007124136 A1 | 11/2007 |
| WO | WO-2007133802 A2 | 11/2007 |

(56) References Cited

FOREIGN PATENT DOCUMENTS

| | | |
|---|---|---|
| WO | WO-2008116024 A2 | 9/2008 |
| WO | WO-2008141057 A1 | 11/2008 |
| WO | WO-2008144326 A2 | 11/2008 |
| WO | WO-2008144665 A1 | 11/2008 |
| WO | 2009035473 A2 | 3/2009 |
| WO | 2009039461 A2 | 3/2009 |
| WO | WO-2009039460 A2 | 3/2009 |
| WO | WO-2010111353 A1 | 9/2010 |
| WO | WO-2011047341 A2 | 4/2011 |
| WO | 2011085216 A2 | 7/2011 |
| WO | WO-2014085362 A1 | 6/2014 |
| WO | WO-2016201373 A1 | 12/2016 |
| WO | WO-2017011767 A2 | 1/2017 |
| WO | WO-2017015272 A1 | 1/2017 |
| WO | WO-2017165635 A1 | 9/2017 |
| WO | WO-2017172757 A1 | 10/2017 |
| WO | WO-2018118626 A1 | 6/2018 |
| WO | WO-2018200977 A1 | 11/2018 |
| WO | WO-2019046167 A1 | 3/2019 |
| WO | WO-2019177973 A1 | 9/2019 |
| WO | WO-2020092618 A1 | 5/2020 |
| WO | WO-2021016369 A1 | 1/2021 |
| WO | WO-2021030607 A1 | 2/2021 |

OTHER PUBLICATIONS

Weintraub et al., 2015, "Clinical spectrum of impulse control disorders in Parkinson's disease," Mov Disord., 30(2):121-127.

International Search Report and Written Opinion of International Patent Application No. PCT/US2018/029831 (published as WO 2018200977) dated Jul. 11, 2018 (10 pages).

"ACP-103," *Drugs of the Future*, Prous Science(2006) vol. 31, No. 11, pp. 939-943.

"NUPLAZID™ (pimavanserin) Sponsor Background Information For A Meeting Of The Psychopharmacologic Drugs Advisory Committee On Mar. 29, 2016," Acadia Pharmaceuticals Inc., 2016. Retrieved from the Internet (URL): <https://www.fda.gov/downloads/advisorycommittees/committeesmeetingmaterials/drugs/psychopharmacologicdrugsadvisorycommittee/ucm492453.pdf> (173 pages).

"Pimavanserin (Nuplazid) for parkinson's disease psychosis," Medical Letter On Drugs And Therapeutics, New Rochelle, NY, US (Jun. 2016) vol. 58, pp. 74-75.

Aarsland et al., "Decreased burden among caregivers of patients with Parkinson's disease psychosis (PDP) treated with pimavanserin, a selective 5-HT2A inverse agonist," (Meeting Abstract) *Neurology*(2015) vol. 84, No. 14, Suppl P6.044.

Abbas et al., "Pimavanserin tartrate: a 5-HT2A inverse agonist with potential for treating various neuropsychiatric disorders," *Expert Opinion on Pharmacotherapy*(2008) vol. 9, No. 18, pp. 3251-3259.

Adam, et al., "Effects of repeated ritanserin on middle-aged poor sleepers," *Psychopharmacology*(1989) 99:219-221.

Aizenstein et al., "Frequent Amyloid Deposition Without Significant Cognitive Impairment Among the Elderly," Arch. Neurol. 65(11):1509-1517 (2008).

Akin, et al., "Decreased serotonin 5-HT 2A receptor-stimulated phosphoinositide signaling in fibroblasts from melancholic depressed patients," *Neuropsychopharmacology*(2004) 29:2081-2087.

Anonymous, "Use of Liquids and/or Soft Foods as Vehicles for Drug Administration: General Considerations for Selection and In Vitro Methods for Product Quality Assessments Guidance for Industry," Jul. 13, 2018 (Jul. 13, 2018), XP055676101, Retrieved from the Internet: URL:https://www.fda.gov/media/114872/downl<http://www.fda.gov/media/114872/downl> oad [retrieved on Mar. 12, 2020].

Antunes, et al., "The novel object recognition memory: neurobiology, test procedure, and its modifications," *Cogn. Process*(2012) 13:93-110.

Bakshi, et al., "Clozapine antagonizes phencyclidine-induced deficits in sensorimotor gating of the startle response," *The Journal of Pharmacology and Experimental Therapeutics*(1994) 271(2):787-794.

Basha, A., "Synthesis of N, N'-disubstituted Ureas from Carbamates," Tetrahedron Letters 29(21): 2525-2526(1988).

Bekris et al. "Cerebrospinal Fluid Ab42 Levels and APP processing pathway genes in Parkinson's disease," Movement Disorders, 2015, vol. 30, No. 7, pp. 936-944, 2015.

Bennett, et al., "Suppression of dyskinesias in advanced Parkinson's disease. II. Increasing daily clozapine doses suppress dyskinesias and improve parkinsonism symptoms," *Neurology*(1993) 43:1551-1554.

Bhana et al., "A Review of its Use in the Management of the Behavioural and Psychological Symptoms of Dementia," Drugs & Aging 16(6):451-471 (2000).

Biagi, et al., "1,2,3-Triazoles: Structural changes on two effective inhibitors of the prostaglandin synthesis in vitro," *Farmaco Ed. Sci.*(1988) 43:597-611.

Bibbiani, et al., "Serotonin 5-HT1A agonist improves motor complications in rodent and primate parkinsonian models," *Neurology*(2001) 57:1829-1834.

Blakley, et al., "Bidirectional changes in ethanol consumption in rats with site-specific antisense down-regulation of 5-hydroxytryptamine2A receptors in brain," *The Journal of Pharmacology and Experimental Therapeutics*(2001) 299(1):277-289.

Blier, et al., "Potential mechanisms of action of atypical antipsychotic medications in treatment-resistant depression and anxiety," *J. Clin. Psychiatry*(2005) 66(suppl 8):30-40.

Blier, et al., "Putative mechanisms of action of antidepressant drugs in affective and anxiety disorders and pain," *Journal of Psychiatry & Neuroscience*(2001) 26(1):37-43.

Bogolubsky et al., "Bis(2,2,2-trifluoroethyl) carbonate as a condensing agent in one-pot parallel synthesis of unsymmetrical aliphatic ureas," (2014), pp. S1-S67. Retrieved from URL: http://pubs.acs.org/doi/suppl/1 0.102 1/co500025f/supl_file co500025f_si_001. pdf, Table S2, pp. S9, entry 47.

Bogolubsky et al., "Bis(2,2,2-trifluoroethyl) carbonate as a condensing agent in one-pot parallel synthesis of unsymmetrical aliphatic ureas," *ACS Combinatorial Science*(2014) vol. 16, Issue 6, pp. 303-308.

Bond et al., "Physiological effects of inverse agonists in transgenic mice with myocardial overexpression of the beta-adrenoceptor," *Nature*(1995) 374:272-276.

Borman et al., "5-HT2B receptors play a key role in mediating the excitatory effects of 5-HT in human colon in vitro," *Br. J. Pharmacol.* (2002) vol. 135, No. 5, pp. 1144-1151.

Brann, M. R. "Identification of ligands by selective amplification of cells transfected with receptors and marker enzymes," *Chemical Abstracts*(1998) 128: 111548.

Buddhala et al. "Correlation between descreased CSF a-synuclein and Ab1-42 in Parkinson disease," Neurobiology of Aging, 2015, vol. 36, pp. 476-484, 2015.

Chaturvedi, D., "Perspectives on the Synthesis of Organic Carbamates," Tetrahedron 68:15-45 (2012).

Chaturvedi, D., "Recent Developments on the Carbamation of Amines," Curr. Org. Chem. 15:1593-1624 (2011).

Choi et al., "5HT2B receptor-mediated serotonin morphogenic functions in mouse cranial neural crest and myocardiac cells," *Development*(1997) vol. 124, pp. 1745-1755.

Cirrito et al., "Serotonin signaling is associated with lower amyloid-p levels and plaques in transgenic mice and humans," *PNAS*(2011) vol. 108, No. 36, p. 14968-14973.

Cummings et al., "Pimavanserin for patients with Parkinson's disease psychosis: a randomised, placebo-controlled phase 3 trial," *Lancet*(2014) vol. 383, pp. 533-540.

Cummings et al., "Pimavanserin: Potential Treatment For Dementia-Related Psychosis." J. Prev. Alzheimers Dis. 5(4): 253-258 (2018).

Database CA [online] Chemical Abstracts Service, Columbus, Ohio, US; 2016, Wang et al., "Intermediate of pimavanserin and its analog, preparation method thereof and preparation method of pimavanserin and its analog," XP002761533, retrieved from STN Database accession No. 2016:451070 (reference date: Mar. 23, 2016).

Database CA [online] Chemical Abstracts Service, Columbus, Ohio, US; 2016, Zheng, Xuchun et al.: "A process for preparing pimavanserin

(56) References Cited

OTHER PUBLICATIONS tartrate," XP002761538, retrieved from STN Database accession No. 2016:1261850 (reference date: Aug. 3, 2016).
Database WPI Week 201622, Derwent Publications Ltd., London, GB; an 2016-17318M, XP002761536 (reference date: Aug. 19, 2015).
Database WPI Week 201623, Derwent Publications Ltd., London, GB; An 2015-708058, XP002761532 (reference date: Oct. 7, 2015).
Database WPI Week 201635, Derwent Publications Ltd., London, GB; an 2016-02257F, XP002761534 (reference date: Dec. 2, 2015).
Database WPI Week 201640, Derwent Publications Ltd., London, GB; an 2016-01442V, XP002761535 (reference date: Dec. 16, 2015).
Database WPI Week 201641, Derwent Publications Ltd., London, GB; an 2016-24419S, XP002761537 (reference date: Apr. 13, 2016).
DeClerck, et al., "Increase in slow-wave sleep in humans with the serotonin-S2 antagonist ritanserin," Current Therapeutic Research (1987) 41(4):427-432.
Delecluse, et al., "A case of tardive tremor successfully treated with clozapine," Movement Disorders(1998) 13(5):846-847.
Dine et al., "One-Pot, Solvent-Free Access to Unsymmetrical Ureas by Palladium-Catalysed Reductive Alkylation Using Molecular Hydrogen," Eur. J. Chem., 5445-5454 (2013).
Dube et al., "Carbonyldiimidazole-Mediated Lossen Rearrangement." Org. Lett. 11 (24):5622-5625 (2009).
Dunn, et al., "Analgetic and antiinflammatory 7-aroylbenzofuran-5-ylacetic acids and 7-aroylbenzothiophene-5-ylacetic acids," J. Med. Chem. (1986) 29:2326-2329.
Durif, et al., "Low-dose clozapine improves dyskinesias in Parkinson's disease," Neurology(1997) 48:658-662.
Eichelbaum, et al., "Influence of pharmacogenetics on drug disposition and response," Clinical and Experimental Pharmacology and Physiology(1996) 23:983-985.
Everett, et al., "L-Dopa: Effect on concentrations of dopamine, norepinephrine, and serotonin in brains of mice," Science(1970) 168:849-850.
Factor, et al. "Clozapine for the treatment of drug-induced psychosis in Parkinson's disease: Results of the 12 week open label extension in the PSYCLOPS trial," Movement Disorders(2001) 16(1):135-139.
Factor, et al., "Clozapine prevents recurrence of psychosis in Parkinson's disease," Movement Disorders(1992) 7(2):125-131.
Fava, M. et al. "A Phase 2, Randomized, Double-Blind, Placebo-Controlled Study of Adjunctive Pimavanserin in Patients with Major Depressive Disorder and an Inadequate Response to Therapy (CLARITY)." J Clin Psychiatry. Sep. 24, 2019;80(6) (13 pages).
Fitzgerald et al., "Possible Role of Valvular Serotonin 5-HT2B Receptors in the Cardiopathy Associated with Fenfluramine," Molecular Pharmacol. (1999) vol. 57, pp. 75-81.
Friedman et al., "A Multi-Center, Placebo-Controlled, Double-Blind Trial To Examine the Safety and Efficacy of Pimavanserin in the Treatment of Psychosis in Parkinson's Disease," Neurology(2010) vol. 74, No. 9, Suppl. 2, pp. A299.
Friedman, et al., "Atypical antipsychotics in the treatment of drug-induced psychosis in Parkinson's disease," Movement Disorders(2000) 15(2):201-211.
Friedman, et al., "Low-dose clozapine for the treatment of drug-induced psychosis in Parkinson's disease," N. Engl. J. Med. (1999) 340(10):757-763.
Friedman, J. H. "Clozapine treatment of psychosis in patients with tardive dystonia: Report of three cases," Movement Disorders(1994) 9(3):321-324.
Gillman, P. K. "Monoamine oxidase inhibitors, opioid analgesics and serotonin toxicity," British Journal of Anaesthesia(2005) 95(4):434-441.
Goldman et al., "Genetic counseling and testing for Alzheimer disease: Joint practice guidelines of the American College of Medical Genetics and the National Society of Genetic Counselors," Genetics in Medicine(2011) vol. 13, No. 6, pp. 597-605.
Hacksell et al., 2014, "On the Discovery and Development of Pimavanserin: A Novel Drug Candidate for Parkinson's Psychosis," Neurochem. Res., vol. 39, pp. 2008-2017.
Han et al., "Synthesis of Carbamates and Ureas Using Zr(IV)-Catalyzed Exchange Processes," Organic Letters 9(8): 1517-1520 (2007).
Hatoum, H. T et al., "The Use of the Occupational Disruptiveness Scale of the Neuropsychiatric Inventory-Nusing Home Version to Measure the Impact of Rivastigmine on the Disruptive Behavior of Nursing Home Residents with Alzheimer's Disease," Journal of the American Medical Directors Association(2005) vol. 6, No. 4, pp. 238-245.
Highlights of Prescribing Information Nuplazid® (pimavanserin), Revised Jun. 2018. Retrieved from the Internet (URL): https://www.accessdata.fda.gov/drugsatfda_docs/label/2018/207318s005lbl.pdf (15 pages).
Highlights of Prescribing Information Nuplazid® (pimavanserin), Revised Mar. 2018. Retrieved from the Internet (URL): https://www.accessdata.fda.gov/drugsatfda_docs/label/2018/207318s002s004lbl.pdf (15 pages).
Idzikowski, et al. 1991. A dose response study examining the effects of ritanserin on human slow wave sleep. Br. J. Clin. Pharmac., 31:193-196.Idzikowski, et al., "A dose response study examining the effects of ritanserin on human slow wave sleep," Br. J. Clin. Pharmac. (1991) 31:193-196.
International Search Report and Written Opinion for International Application No. PCT/US2013/071792, dated, Jan. 1, 2014 (9 pages).
International Search Report and Written Opinion in corresponding PCT Application PCT/US2016/042933 dated Oct. 14, 2016 (13 pages).
International Search Report and Written Opinion in corresponding PCT Patent Application No. PCT/US08/057557 dated Oct. 24, 2008 (10 pages).
International Search Report and Written Opinion in corresponding PCT Patent Application No. PCT/US2017/023795 dated May 29, 2017 (11 pages).
International Search Report and Written Opinion in corresponding PCT Patent Application No. PCT/US2017/024526 dated Jul. 5, 2017 (18 pages).
International Search Report and Written Opinion in corresponding PCT Patent Application No. PCT/US2017/066340 dated Mar. 5, 2018 (13 pages).
International Search Report and Written Opinion in corresponding PCT Patent Application No. PCT/US2018/048096 dated Oct. 30, 2018 (12 pages).
International Search Report and Written Opinion of the International Searching Authority for International Application No. PCT/US2019/021618 dated Jun. 12, 2019 (10 pages).
International Search Report and Written Opinion of the International Searching Authority for International Application No. PCT/US2019/058927 dated Jan. 23, 2020 (16 pages).
International Search Report and Written Opinion of the International Searching Authority for International Application No. PCT/US2020/043103 dated Dec. 18, 2020 (12 pages).
International Search Report and Written Opinion of the International Searching Authority for International Application No. PCT/US2020/46212 dated Oct. 23, 2020 (10 pages).
International-type Search Report by International Searching Authority for SE1630067-5 dated Sep. 23, 2016 (18 pages).
Ito et al., "Prediction of Human Drug Clearance from in Vitro and Preclinical Data Using Physiologically Based and Empirical Approaches," Pharm. Res., (2005) vol. 22, No. 1, pp. 103-112.
Kalgutkar, et al., "Selective inhibitors of monoamine oxidase (MAO-A and MAO-B) as probes of its catalytic site and mechanism," Medicinal Research Reviews (1995) 15(4)325-388.
Katritzky et al., Chapter V. "Reaction of Amines with Carbamic Acid Esters," Comprehensive Organic Functional Group Transmformations, pp. 501-502 (1995).
Kondo et al., "Novel Ruthenium-Complex Catalyzed Synthesis of Ureas from Formamides and Amines," Organometallics 16:2562-2570 (1997).

(56) References Cited

OTHER PUBLICATIONS

Kotachi et al., "Ruthenium catalysed N.N'-Diarylurea Synthesis from N-Aryl Substituted Formamides and Aminoarenes," J. Chem. Soc., Chem. Comm., 7:549-550 (1990).
Lane et al., "Alzheimer's Disease," Eur. J. Neurol. 25:59-70 (2018).
Lashley et al. "Cortical a-synuclein load is associated with amyloid-b plaque burden in subset of Parkinson disease patients," Acta Neuropathol. 2008, 115, 417-425.
Leysen, et al. "Serotonergic component of neuroleptic receptors," *Nature*(1978) 272:168-171.
Liechti, et al., "Effects of MDMA (ecstasy) on prepulse inhibition and habituation of startle in humans after pretreatment with Citalopram, Haloperidol, or Ketanserin," *Neuropsychopharmacology*(2001) 24(3):240-252.
Linder, et al. "Pharmacogenetics: A laboratory tool for optimizing therapeutic efficiency," *Clinical Chemistry*(1997) 43(2):254-266.
Loudon et al., "Conversion of Aliphatic Amides into Amines with [I,I-Bis(trifluoroacetoxy)iodo]benzene. 1. Scope of Reaction," J. Org. Chem. 49:4272-4276 (1984).
Marek et al., "The Selective 5-HT2A receptor Antagonist MI00907 Enhances Antidepressant-Like Behavioral Effects of the SSRI Fluoxetine," *Neuropsychopharmacology*(2005) vol. 30, No. 12, pp. 2205-2215.
Marek, et al., "Synergistic action of 5-HT2A antagonists and selective serotonin reuptake inhibitors in neuropsychiatric disorders," *Neuropsychopharmacology*(2003) 28:402-412.
Matsumura et al., "A New Method for Synthesis of Unsymmetrical Ureas Using Electochemically Prepared Trifluoroethyl Carbamates," J. Org. Chem. 65:1549-1551 (2000).
Yoshimura et al., (Tosylimino)phenyl-λ3-iodane as a Reagent for the Synthesis of Metyl Carbamates via Hofmann Rearrangement of Aromatic and Aliphatic Carboxamides, Journal of Organic Chemistry 77:2087-2091 (2012).
Medical Review(s), Application No. 207318prig1s000, Center for Drug Evaluation and Research, Submission Date Sep. 1, 2015 [available online Jun. 3, 2016]. Retrieved from the Internet (URL): <https://www.accessdata.fda.gov/druasatfda_docs/nda/2016/207318Orig1s000MedR.pdf> (173 pages).
Meltzer et al., "Co-therapy with pimavanserin and risperidone 2 mg provides an improved clinical profile," *Schizophrenia Research*(2008) vol. 98, pp. 16.
Meltzer et al., "Pimavanserin, a Serotonin(2A) Receptor Inverse Agonist, for the Treatment of Parkinson's Disease Psychosis," *Neuropsychopharmacology*(2010) vol. 35, No. 4, pp. 881-892.
Meltzer et al., "Serotonin Receptors: Their Key Role in Drugs to Treat Schizophrenia," *Progress in Neuro-Pyschopharmacology & Biol. Psych.* (2003) vol. 27, pp. 1159-1172.
Meltzer, et al., "Plasma clozapine levels and the treatment of L-DOPA-induced psychosis in Parkinson's disease," *Neuropsychopharmacology*(1995) 12(1):39-45.
Meltzer, H. Y. "The role of serotonin in antipsychotic drug action," *Neuropsychopharmacology*(1999)21(2S):106S-115S.
Morley et al., "Antibody to Amyloid p Protein Alleviates Imparied Acquisition, Retention, and Memory Processing in SAMP8 Mice," *Neurobiology of Learning and Memory*(2002), 78(1 ):125-138.
Naritomi et al., "Prediction of human hepatic clearance from in vivo animal experiments and in vitro metabolic studies with liver microsomes from animals and humans," *Drug Metab. Dispos.* (2001) vol. 29, No. 10, pp. 1316-1324.
NDA Approval/Supplement Approval, NDA 210793 NDA 207318/S-003, Letter Signed Jun. 28, 2018. Retrieved from the Internet (URL): https://www.accessdata.fda.gov/drugsatfda_docs/appletter/2018/2107930rig1s000,2073180rig1s 003ltr.pdf (5 pages).
Nebigil et al., "Serotonin is a novel survival factor of cardiomyocytes: mitochondria as a tarqet of 5-HT2B-receptor signaling," *FASEB J.* (2003) vol. 27, No. 10, pp. 1373-1375.
Ng, et al., "L-dopa-induced release of cerebral monoamines," *Science*(1970) 170:76-77.

Nordstrom, et al., "High 5-HT2 receptor occupancy in clozapine treated patients demonstrated by PET," *Psychopharmacology*(1993) 110:365-367.
Norton et al., "Caregivers of PDP patients have an increased risk of developing emotional and social distress that is decreased when PDP is treated with pimavanserin," (Meeting Abstract) *Journal of Parkinson's Disease*(Sep. 2016) vol. 6, No. S1, pp. 257, Abstract No. P42.11.
Norton et al., "Decreased burden among caregivers of patients with Parkinson's disease psychosis (PDP) treated with pimavanserin, a selective 5-HT2A inverse agonist," (Meeting Abstract) *Journal of Parkinson's Disease*(Sep. 2016) vol. 6, No. S1, p. 88, Abstract No. P12.08.
Obach et al., "The Prediction of Human Pharmacokinetic Parameters from Preclinical and In Vitro Metabolism Data," *J. Pharm. Exp. Therap.* (1997) vol. 283, No. 1, pp. 46-58.
Ogawa, et al., "Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis," *European Journal of Pharmacology*(2005) 521:156-163.
Paiva, et al., "Effects of ritanserin on sleep disturbances of dysthymic patients," *Psychopharmacology*(1988) 96:395-399.
Patel, et al., "The highly selective 5-hydroxytryptamine (5-HT)2A receptor antagonist, EMO 281014, significantly increases swimming and decreases immobility in male congenital learned helpless rats in the forced swim test," *Synapse*(2004) 52:73-75.
Pierce, et al., "5-hydroxytryptamine-induced synovial plasma extravasation is mediated via 5-hydroxytryptamine2A receptors on sympathetic efferent terminals," *The Journal of Pharmacology and Experimental Therapeutics*(1995) 275(1):502-508.
Poewe, W. "Psychosis in Parkinson's disease," *Movement Disorders*(2006) vol. 18, Suppl. 6, pp. S80-S87.
Pollak, et al., "Clozapine in drug-induced psychosis in Parkinson's disease," *Lancet*(1999) 353:2041-2042.
Price et al., "Pimavanserin, a 5-HT2A receptor inverse agonist, reverses psychosis-like behaviors in a rodent model of Alzheimer's disease," *Behavioural Pharmacology*(2002), 23:426-433.
R&D Focus Drug News (Jan. 24, 2000). Pimvaserin ACADIA lead compounds identified.
R&D Focus Drug News (Nov. 12, 2001). Pimvaserin ACADIA preclinical data.
Sadzot, et al., "Hallucinogenic drug interactions at human brain 5-HT2 receptors: Implications for treating LSD-induced hallucinogenesis," *Psychopharmacology*98:495-499.
Saltzman, et al., "Cloning of the human serotonin 5-HT2 and 5-HT1C receptor subtypes," *Biochemical and Biophysical Research Communications*(1991) 181(3):1469-1478.
Sandler and Karo, Chapter E., "Reaction of Amines with Urethanes and Carbamates," Organic Functional Group Preparations, Academic Press pp. 161-162 (1986).
Satori and Maggi, "Acyclic and Cyclic Ureas," Science of Synthesis 18: 695-699 (2005).
Saxena, et al., "Cardiovascular effects of serotonin agonists and antagonists," *Journal of Cardiovascular Pharmacology*(1990) 15(Supp. 7):S17-S34.
Shanmugam, S. "Granulation Techniques and Technologies: Recent Progresses," *BioImpacts*(2015) vol. 5, No. 1, pp. 55-63.
Stoner et al., "Integrated oral bioavailability projection using in vitro screening data as a selection tool in drug discovery," *Int. J. Pharm.* (2004) vol. 269, No. 1, pp. 241-249.
Swedish Search Report for Patent Application No. 1730232-4 dated Mar. 28, 2018 (10 pages).
Thavonekham, "A Practical Synthesis of Ureas from Phenyl Carbamates," Synthesis 11:1189-1194(1997).
Vanover et al., "Pharmacological Characterization of AC-90179 [2-( 4-Methoxy-phenyl)-N-( 4-methyl-benzyl)-N-( 1-methyl-piperidiny-4-yl)-acetamide Hydrochloride]: A Selective Serotonin 2A Receptor Inverse Agonist," *J. Pharmacology & Experimental Therapeutics*(2004) vol. 310, No. 3, pp. 943-951.

(56) References Cited

OTHER PUBLICATIONS

Vinogradova et al., Palladium Catalyzed Cross-Coupling of Aryl Chlorides and Triflates with Socium Cyanate: A Practical Synthesis of Unsymmetrical Ureas, J. Am. Chem. Soc. 134:11132-11135 (2012).
Volk et al., "Synthesis of methyl ethyl and phenyl 4 2 methylpropoxy benzyl carbamates," The IP.com Prior Art Database, Disclosure No. IPCOM000244271D, (Nov. 27, 2015).
Ye et al. "Improving response inhibition in Parkinson's disease with Atomoxetine." Biological Psychiatry, Apr. 15, 2015, 77, 740-748.
Yoshimura et al., "Hypervalent Iodine Catalyzed Hofmann Rearrangement of Carboxamides Using Oxone as Terminal Oxidant," JOC 77:11399-11404 (2012).

\* cited by examiner

PIMAVANSERIN FOR TREATING IMPULSE CONTROL DISORDER

CROSS REFERENCE

This application is a U.S. National Stage Application of International Patent Application No. PCT/US2018/029831, filed Apr. 27, 2018, which claims the benefit of priority of U.S. Provisional Patent Application No. 62/491,820, filed Apr. 28, 2017, the content of each of which is incorporated by reference herein in its entirety.

The present disclosure relates generally to therapeutic use of pimavanserin or a pharmaceutical acceptable salt thereof. More specifically, the present disclosure provides methods for treating a disease or disorder by administering pimavanserin or a pharmaceutical acceptable salt thereof to a patient having impulse control disorder.

BACKGROUND

New and effective pharmacological treatments for psychiatric disorders continue to be an area of intense research. Impulse control disorder (ICD) a psychiatric disorder categorized in Diagnostic and Statistical Manual of Mental Disorders (DSM) fourth edition (herein referred to as DSM-5)

ICD is often recognized by impulsivity, e.g. failure to resist a temptation, drive, urge or temptation to perform act that is harmful to oneself or others. There are several aspect of impulsivity, and it is generally believed there are five behavioural stages characterize impulsivity: an impulse, growing tension, pleasure on acting, relief from the urge and finally guilt (which may or may not arise). It is recognized that impulsivity is a features in many psychiatric disorders such as attention deficit hyperactivity disorder (ADHD), substance-related disorders (e.g. cocaine abuse etc), mood disorders, and borderline personality disorders etc.

Current literatures suggests that serotonergic control play a role in impulsivity, see, e.g., Cunningham, Neuropharmacology, 2014, vol. 76, pages 460-478.

Pimavanserin (formerly ACP-103) is a potent and selective 5-hydroxytryptamine (5-HT)$_{2A}$ receptor inverse agonist of interest as therapeutic for neuropsychiatric diseases and disorders, such as, for example, Parkinson's disease psychosis, sleep disorders, and schizophrenia. See, e.g., U.S. Pat. No. 7,601,740 B2; Vanover et al., The Journal of Pharmacology and Experimental Therapeutics, 2006, vol. 317, no. 2, pages 910-918. Preparations of pimavanserin and pimavanserin in salt and crystalline forms have been described in, for instance, U.S. Pat. No. 7,601,740 B2, WO 2006/037043 A1 and WO 2006/036874 A1. Tolerability and safety of pimavanserin has been studied in healthy volunteers, see, e.g., Vanover et al., The Journal of Clinical Pharmacology, 2007, vol. 47, no. 6, pages 704-714, and clinical studies with pimavanserin have been undertaken.

A demand exists for new mono- and combination therapies for treatments of ICD as there is evidence that ICD is under-recognized and undertreated, Weintraub et al., Movement Disorders, 2015, vol. 30, pages 121-127.

SUMMARY

Provided herein are methods for therapeutic use of pimavanserin or a pharmaceutically acceptable salt thereof. More specifically, the present disclosure provides methods for treating a disease or disorder by administering pimavanserin or a pharmaceutical acceptable salt thereof to a patient who has an impulse control disorder.

In one aspect, provided herein is a method for treating an impulse control disorder in a patient comprising administering to the patient a compound of Formula (I) or a pharmaceutically acceptable salt thereof:

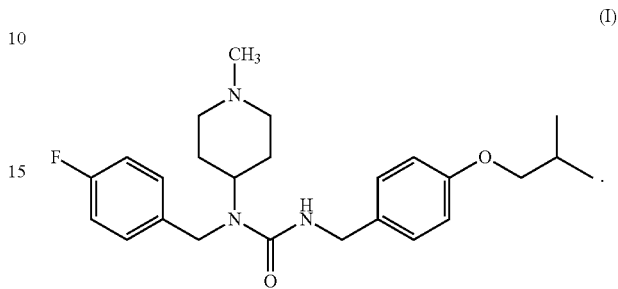

(I)

In another aspect, provided herein is compound of Formula (I) or a pharmaceutical acceptable salt thereof:

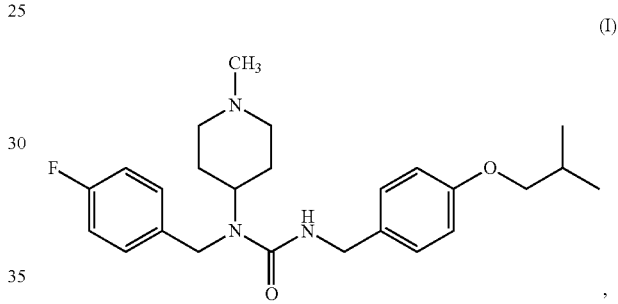

(I)

for treating an impulse control disorder.

In some specific embodiments, the impulse treated is selected from the group consisting of hypersexuality, gambling, buying, eating, punding, hobbyism, walkabout, hoarding, dopamine dysregulation syndrome and addiction.

In some specific embodiments, the impulse treated is selected from the group consisting of hypersexuality, gambling, buying, and eating, for example pathological gambling, the buying is compulsive buying and eating is binge-eating disorder (BED).

In some embodiments pimavanserin is administered to a patient, optionally undergoing Parkinson's treatment, to treat hypersexuality.

In some embodiments pimavanserin is administered to a patient, optionally undergoing Parkinson's treatment, to treat compulsive gambling.

In some embodiments pimavanserin is administered to a patient, optionally undergoing Parkinson's treatment, to treat compulsive buying.

In some embodiments pimavanserin is administered to a patient, optionally undergoing Parkinson's treatment, to treat compulsive eating, such as binge-eating disorder.

In some specific embodiments, the patient has been diagnosed with Parkinson's disease.

In some specific embodiments, the patient is on dopamine replacement therapy (DRT) or administered a dopamine agonist. In other embodiment the patient is subject to a dose change of the dopamine replacement therapy or dopamine agonist.

In other embodiments, the dose of the compound of Formula (I) is an effective daily dose. The effective daily dose may be selected from the group consisting of 8.5, 10, 12, 15, 17, 20, 22, 25, 30, and 34 mg of the compound of Formula (I). In some embodiments the daily dose is selected from 17 mg and 34 mg of pimavanserin.

In other embodiments, the compound of Formula (I) is administered as a tartrate salt.

In other embodiments, an effective daily amount of the compound of Formula (I) as a tartrate salt is administered. Example of effective doses of the tartrate salt of the compound of Formula (I) are 10, 15, 20, 25, 20, 35, and 40 mg. In some embodiments the daily dose is selected from 20 mg and 40 mg of pimavanserin tartrate.

In some embodiments, a pharmaceutical salt of the compound of Formula (I) is administered to the patient. In some specific embodiments, a tartrate salt of the compound of Formula (I) is administered to the patient.

In some embodiments, the tartrate salt of the compound of Formula (I) is administered daily. In some embodiments, the tartrate salt of compound of Formula (I) is administered once daily. In some embodiments, the tartrate salt of compound of Formula (I) is formulated for oral administration as a unit dose. In a specific embodiment, the unit dose is a tablet.

In some embodiments, the tartrate salt of the compound of Formula (I) is in a crystalline form, wherein the crystalline form of the tartrate salt of the compound of Formula (I) exhibits a X-ray powder diffraction pattern comprising peaks having d-values in angstroms of about 10.7, about 4.84, about 4.57, and about 3.77.

DETAILED DESCRIPTION

The present disclosure provides methods for treating impulse control disorder (ICD) by administering pimavanserin or a pharmaceutical acceptable salt thereof to a patient.

Aspects of ICD have been connected to various diseases and can be very troublesome to the patient as well as the caregiver, depending on what type of impulse control. The present disclosure primarily relates to hypersexuality/compulsive sexual behaviour, and related behavior such as paraphilia, zoophilia with devastating consequences; gambling, such as inappropriate and maladaptive gaming behavior, such as repetitive slot machines, lottery or scratch cards and internet gambling; buying, eating, such as binge eating disorder; punding, such as repetitive and stereotyped non-goal-oriented behavior, characterized by an intense preoccupation with items or activities; hobbyism, such as the compulsive pursuit of a hobby such as collecting, cleaning or excessive internet use; walkabout, such as excessive, aimless wandering, hoarding, such as collecting and failure to discard items without objective value, dopamine dysregulation syndrome, such as misuse and escalating dose of medication, and addiction. The present disclosure relates to the method of treatment of ICD, and for example to the treatment of hypersexuality, gambling, buying, eating, punding, hobbyism, walkabout, dopamine dysregulation syndrome and addiction. The present disclosure relates to pimavanserin for treating hypersexuality, gambling, buying, eating, punding, hobbyism, walkabout, hoarding, dopamine dysregulation syndrome and addiction.

One particular disease where ICD can be particular troublesome is Parkinson's disease (PD) where patients may experience impulse control disorders (ICDs) when on dopamine agonist therapy, and optionally when on DRT, for their motor symptoms. ICDs include behaviors such as pathological gambling, hypersexuality, binge eating and excessive or compulsive shopping as discussed above, any or all of which negatively impacts the quality of life of the patients (Voon et al., Lancet Neurol., 2009, 8(12):1140-9). The emergence of these disorders can have an exceedingly grave impact on the quality of life for the families and care takers as well as the affected PD patient.

ICD prevalence is significantly increased in PD patients by the dopamine replacement therapies (DRTs) these patients require to control their motor symptoms (Weintraub et al. Impulse control disorders in Parkinson disease: a cross-sectional study of 3090 patients. Arch. Neurol. 67, 589-595). This represents a treatment dilemma for physicians treating PD patients because controlling one set of symptoms frequently leads to worsening another set of symptoms. Therefore, there exists a need for medications that treat motor deficits but do not induce ICDs. In the absence of such medications, relevant alternatives include adjunct treatments that can mitigate established ICDs, without impacting the capacity of a dopamine agonist to improve motor symptoms in PD patients. Candidates for such medications include selective 5-HT2A inverse agonists such as pimavanserin (Nuplazid™, ACP-103), which has been shown to control hallucinations and delusions associated with PD without impacting motor function in those patients (Cummings et al., vol. 383, No. 9916, pages 533-540, published online 2013).

In one aspect pimavanserin is used to effectively treat one or more of the following: compulsive or pathological gambling, eating, buying and sexual behaviours.

In some aspects the compulsive or pathological gambling, eating, buying and sexual behaviours is in a Parkinson's disease patient.

In some aspects the compulsive or pathological gambling, eating, buying and sexual behaviours is in a Parkinson's disease patient currently undergoing Parkinson treatment. In some aspects the Parkinson treatment is a dopamine replacement therapy or the patient is administered a dopamine agonist. The following is a non-exhaustive list comprising examples of dopamine agonist: pramipexole, ropinirole, rotigotine, apomorphine, bromocriptine, cabergoline, ciladopa, dihydrexidine, dinapsoline, doxanthrine, epicritine, lisuride, pergolide, piribedil, propylnorapomorphine, quinagolide, roxindole, and sumanirole. In some aspects the compulsive or pathological gambling, eating, buying and sexual behaviours is in a Parkinson's disease patient currently undergoing Parkinson treatment are considered a side effect of the administration of a DRT (e.g. levodopa/carbidopa) or the dopamine agonist, e.g. pramipexole, ropinirole, rotigotine, apomorphine, bromocriptine, cabergoline, ciladopa, dihydrexidine, dinapsoline, doxanthrine, epicritine, lisuride, pergolide, piribedil, propylnorapomorphine, quinagolide, roxindole, and sumanirole.

In some aspects the compulsive or pathological gambling, eating, buying and sexual behaviours is in a Parkinson's disease patient currently not undergoing Parkinson treatment.

In some aspects the ICD is in a patient having Parkinson's disease.

In some aspects the administration of pimavanserin to treat ICD does not impair motor function nor interfere with dopamine replacement therapies in a patient having Parkinson's disease.

In some aspects the ICD is in a patient not having Parkinson's disease.

In some aspects the ICD is in a patient having Tourettes syndrome.

In some aspects the ICD is in a patient not having Tourettes syndrome.

The ICDs, mentioned herein above can be screened using different techniques, for example the Minnesota Impulsive Disorders Interview (MIDI) can be used to screen buying and eating behaviours, Massachusetts Gambling screen (MAGS) may be used to screen gambling behaviour, and Diagnostic and statistical manual of mental disorders 5$^{th}$ edition (DSM-5) can be used to screen eating disorders.

In some aspects the screening for gambling, eating, buying and sexual behaviours is done using Questionnaire for Impulsive-Compulsive Disorders in Parkinson's disease (QUIP). In some aspects the patient is rated using the Questionnaire for Impulsive-Compulsive Disorders in Parkinson's disease rating scale (QUIP-RS). The QUIP-RS is a validated, reliable clinical questionnaire to assess the severity of ICD in PD. Seven dimensions of ICD over the 4 past weeks are assessed through 4 questions: Gambling; Buying; Eating; and Sexual Behavior, leading to the total ICD score from 0 (normal) to 64 (most abnormal). The questionnaire also assesses Hobbyism; Punding and Medication use, that, when added to the former 4 ICD correspond to the total QUIP-RS score from 0 to 112

In some aspects pimavanserin is used to treat one or more of the compulsive or pathological gambling, eating, buying and sexual behaviours is in a Parkinson's disease patient, and evaluated using the total ICD score using Questionnaire for Impulsive-Compulsive Disorders in Parkinson's Disease-Rating Scale (QUIP-RS). In some aspect the total ICD score after at least 4 weeks is at least −10, such as at least −12, −14, −15, −16, −17, −18, −19, or −20, compared to the total ICD score at week zero (prior to administration of pimavanserin).

In some aspects pimavanserin is administered to a Parkinson's disease patient during 4 weeks and wherein the patient receives a total ICD score of at least −10, such as at least −12, −14, −16, −17, −18, −19, or −20, compared to the total ICD score at week zero.

In some aspects pimavanserin is administered during 4 weeks to a Parkinson's disease patient, currently undergoing Parkinson treatment, wherein the patient after receiving pimavanserin for 4 weeks receives a total ICD score of at least −10, such as at least −12, −15, −16, −17, −18, −19, or −20, compared to the total ICD score at week zero.

In some aspects pimavanserin is administered in a daily dose of 40 mg pimavanserin tartrate to a Parkinson's disease patient, currently undergoing Parkinson treatment, during 4 weeks and wherein the patient receives a total ICD score of at least −10, such as at least −12, −14, −15, −16, −17, −18, −19, or −20, compared to the total ICD score at week zero.

In some aspects pimavanserin is administered to a Parkinson's disease patient during 8 weeks and wherein the patient receives a total ICD score of at least −10, such as at least −12, −14, −15, −16, −17, −18, −19, or −20, compared to the total ICD score at week zero.

In some aspects pimavanserin is administered during 8 weeks to a Parkinson's disease patient, currently undergoing Parkinson treatment, and wherein the patient after receiving pimavanserin for 8 weeks receives a total ICD score of at least −10, such as at least −12, −14, −15, −16, −17, −18, −19, or −20, compared to the total ICD score at week zero.

In some aspects a daily dose of 34 mg pimavanserin is administered during 8 weeks to a Parkinson's disease patient, currently undergoing Parkinson treatment, wherein the patient after receiving pimavanserin for 8 weeks receives a total ICD score of at least −10, such as at least −12, −14, −15, −16, −17, −18, −19, or −20, compared to the total ICD score at week zero.

In some aspects the Parkinson treatment is dopamine replacement therapy.

In some aspects the Parkinson treatment is administration of a dopamine agonist.

In some aspects the patient has been diagnosed with Parkinson's disease and is undergoing treatment for the disease. Examples of treatments are dopamine replacement therapy and dopamine agonist.

In some aspect the patient undergoing Parkinson's disease treatment is subject to a change in the dopamine replacements therapy, for example a dose adjustment.

In some aspect the patient undergoing Parkinson's disease treatment is subject to a change in the administration of the dopamine agonist, for example a dose adjustment, such as an increased dose (e.g. as the disease progress and motor symptoms become worse).

A Parkinson's disease patient, subject to a change in the Parkinson's disease treatment (e.g. because the disease progress and motor symptoms become worse), may develop an impulse control, e.g. one or more of the compulsive or pathological gambling, eating, buying and sexual behaviours. The change in the treatment, for example an increased dose of a dopamine agonist, may result in the patient developing one or more impulse control such as compulsive or pathological gambling, eating, buying and sexual behaviours. In some aspects pimavanserin is administered to treat the impulse control that may be the result of the change in the Parkinson's disease treatment, for example an increased dose of the currently administered dopamine agonist.

In some aspects pimavanserin and a dopamine agonist are co-administered to a Parkinsons's disease patient.

Pimavanserin is N-(1-methylpiperidin-4-yl)-N-(4-fluorophenylmethyl)-N'-(4-(2-methylpropyloxy)phenylmethyl) carbamide, and has the structure of Formula (I):

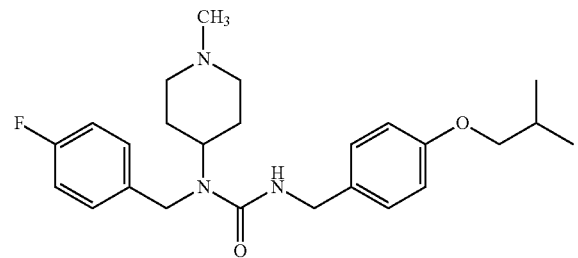

(I)

Pimavanserin may be synthesized by methods described in U.S. Pat. No. 7,601,740 (see columns 22-26), which is incorporated herein by reference in its entirety. In a specific embodiment, pimavanserin is prepared as shown in Scheme I below, or by modification of these methods. Ways of modifying the methodology include, among others, modification in temperature, solvent, reagents, etc., as will be known those skilled in the art.

Pimavanserin can be present in a number of salts and crystalline forms which are included in the present disclosure.

Exemplary salts include the tartrate, hemi-tartrate, citrate, fumarate, maleate, malate, phosphate, succinate, sulphate, and edisylate (ethanedisulfonate) salts. Pimavanserin salts including the aforementioned ions, among others, are described in U.S. Pat. No. 7,868,176, which is incorporated herein by reference in its entirety.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

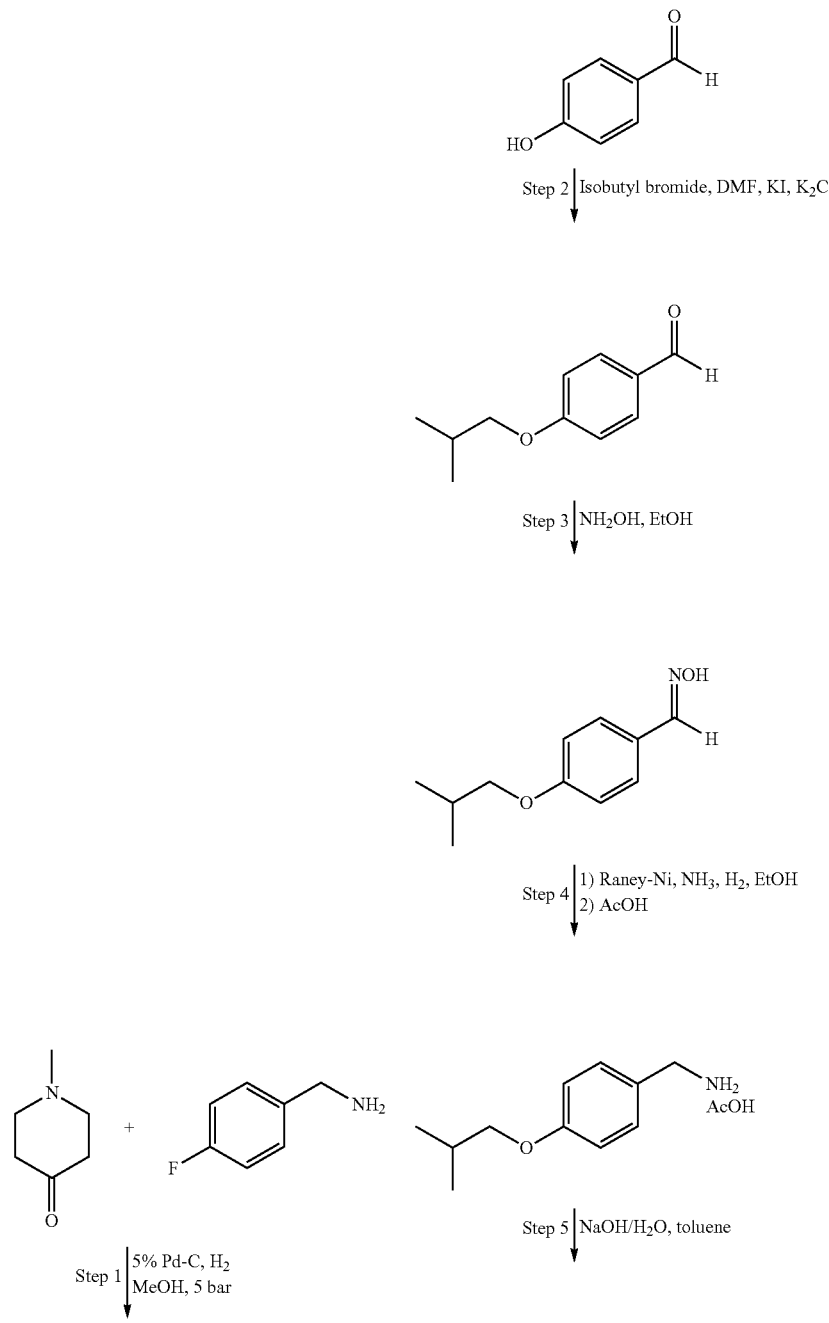

Scheme 1: Synthesis of Pimavanserin

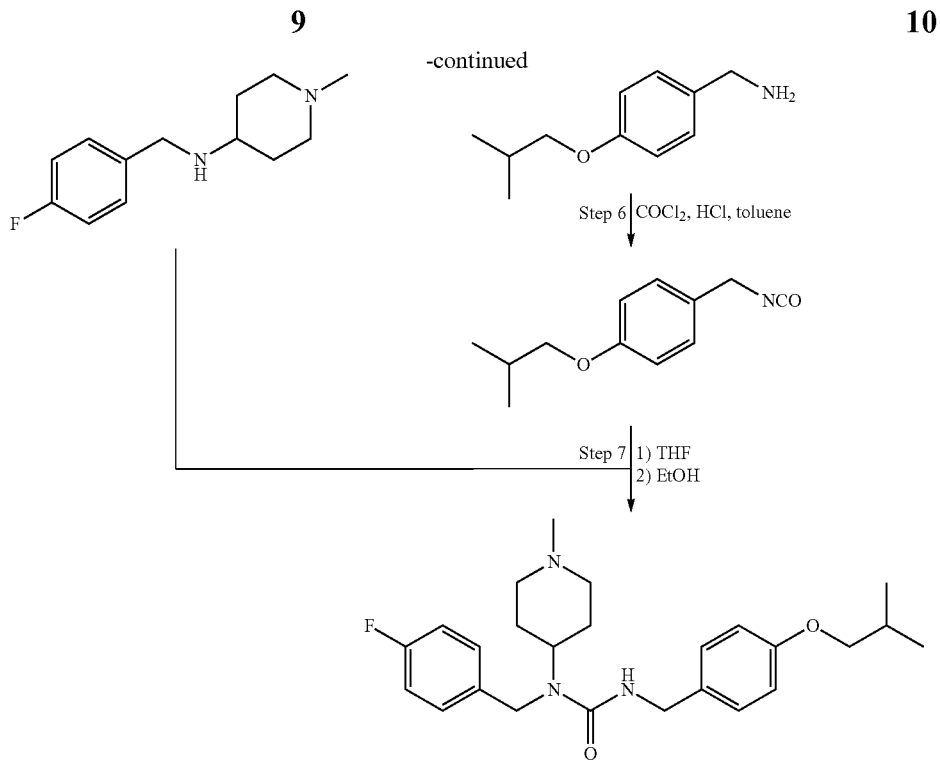

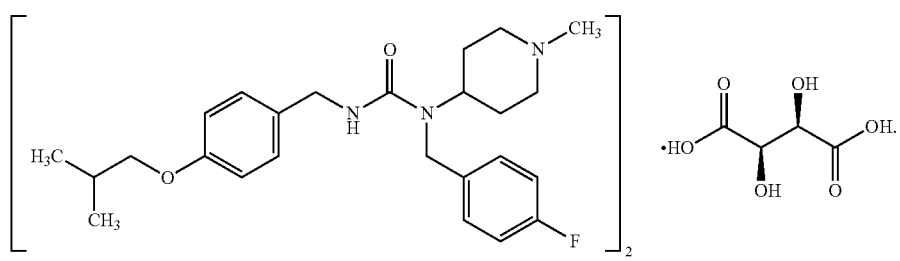

In certain embodiments, the pharmaceutically acceptable salt of pimavanserin is a tartrate salt of pimavanserin. In some embodiments, the pimavanserin tartrate salt can, for example, be urea, N-[(4-fluorophenyl)methyl]-N-(1-methyl-4-piperidinyl)-N'-[[4-(2-methylpropoxy)phenyl]methyl]-, (2R,3R)-2,3-dihydroxybutanedioate (2:1), which has the following chemical structure:

Several crystalline forms of the tartrate salt are referred to as crystalline Form A, Form B, Form C, Form D, Form E and Form F, and are described in U.S. Pat. No. 7,732,615, which is incorporated herein by reference in its entirety. In one embodiment, the crystalline form of the tartrate salt of pimavanserin is Form C, which exhibits an X-ray powder diffraction pattern comprising peaks having d-values in angstroms of about 10.7, about 4.84, about 4.57, and about 3.77. Specifically the X-ray powder diffraction pattern of Form C exhibits the following characteristic peaks expressed in d-values (Å): 12.0 (w), 10.7 (vs), 7.4 (vw), 6.9 (vw), 6.6 (vw), 6.2 (w), 5.86 (m), 5.53 (w), 5.28 (m), 5.16 (m), 4.84 (vs), 4.70 (m), 4.57 (s), 4.38 (m), 4.09 (w), 3.94 (w), 3.77 (s), 3.71 (m), 3.49 (w), 3.46 (w), 3.25 (w), 3.08 (w), and 2.93 (w). In various embodiments, Form C is present in a solid form of pimavanserin in amounts of at least about 50%, 70%, 80%, 90%, 95%, or 98%, with the remainder being other crystalline forms (including hydrates and solvates) and/or amorphous forms.

Pimavanserin (including, for example, the tartrate salt) may be formulated into tablets, such as is described in more detail in U.S. Pat. No. 7,790,899, and U.S. Patent Publication No. 2007-0264330, filed May 15, 2007, each entitled "PHARMACEUTICAL FORMULATIONS OF PIMAVANSERIN," which are incorporated herein by reference in their entireties.

The methods and the compositions provided herein can be used to treat various aspects of impulse control disorders treatable by pimavanserin or a pharmaceutically acceptable salt thereof, such as a psychiatric disorder, a neurodegenerative disorder, and a condition induced by treatment of a psychiatric or neurodegenerative disorder. Many psychiatric disorders feature impulsivity including substance-related disorders, attention deficit hyperactivity disorder, antisocial personality disorder, borderline personality disorder, conduct disorder and mood disorders.

In some embodiments, the impulse control disorder is associated with Parkinson's disease or the treatment thereof.

In some embodiments, a pharmaceutical salt of pimavanserin is administered to the patient. In some specific embodiments, a tartrate salt of pimavanserin is administered to the patient.

The exact route of administration, dose, or frequency of administration would be readily determined by those skilled in the art and can be dependent on the age, weight, general physical condition, or other clinical symptoms specific to the patient to be treated.

In some embodiments, the tartrate salt of pimavanserin is administered daily. In some embodiments, the tartrate salt of pimavanserin is administered once daily. In some embodiments, the tartrate salt of pimavanserin is formulated for oral administration as a unit dose. In a specific embodiment, the unit dose is a tablet.

EXAMPLES

Example of a pimavanserin study relating to binge eating disorder (BED)

The criteria for a diagnosis of BED includes (1) eating much more rapidly than normal, (2) eating large amounts of food when not feeling physically hungry, and (3) eating until feeling uncomfortably full (Association Diagnostic and Statistical Manual of Mental Disorders, Fifth Edition (DSM-5), 2013).

Carbohydrate and fat 'comfort foods', with bingeing on chocolate are known to be associated with eating disorders in humans and in rodents. Robust binge-eating behaviour can be induced in rats by giving them time-limited periods to consume highly palatable foods using an unpredictable, intermittent presentation schedule over an extended period of time (weeks) and without restricting their ability to consume normal chow and water (Corwin et al, Binge-type eating induced by limited access in rats does not require energy restriction on the previous day. Appetite 42: 139-142, 2004).

Rats will then avidly consume excessive amounts of the palatable food during the sessions they receive access, with compensatory reductions of normal chow intake in these sessions and the days thereafter.

BED is, for example, to be studied using lean, female, Wistar rats (weight range 200-250 g at the start of the study) from Charles River, UK. Rats are to be contained in a controlled environment and housed in an appropriate way to perform the study, for example singly-housed in polypropylene cages with wire grid floors to enable food intake of each rat to be recorded.

Establishment of binge-eating behavior in rats:

With each cohort of animals in a binge-eating study (cohorts of rats (N=5 to 10 per group) to be used in the study including groups of binge-eating and non-binge-eating controls; rats receiving test drug or vehicle), rats are to be trained to binge on chocolate for at least three weeks and randomized to pimavanserin treatment on the basis of body weight, food and water intake and the size of the previous binge meal.

Body weight, food and water intake are to be measured each day throughout the study, for example as described in the following: Animals are to be weighed at weekly intervals after arrival. After a two-week acclimatization period, animals are to be allocated into treatment groups based on body weight. All animals shall have 24 h ad libitum access to standard powdered diet (e.g. Harlan Teklad 2018; 13.0 kJ/g) and tap water throughout the study. The diet may be contained in a glass feeding jar with an aluminium lid (e.g. Solmedia Laboratory Suppliers, Romford, Essex, UK), allowing access to the food. On binge days, an additional jar containing chocolate (23.44 kJ/g) or an empty jar (control) is to be placed in each cage for a 2 h period, (optionally other suitable time intervals may be used), on Days 1, 2, 4, 6, 7, 9, 12, 14, 15, 18, 23 and 28 (optionally other similar randomly spaced, intermittent, and progressively longer time intervals may be used). The interval between the binge sessions are to be gradually increased as the training progress. Once the rats showed robust, reproducible binge-eating, the binge-eating behaviour can be maintained by giving the rats only one or two binge sessions per week. The jars are to be placed in the cages at ~10:30 h, which was at the beginning of the dark phase for the rats. The weights of the jars are to be recorded before and after the 2 h test session. Hence, the binge-eating sessions are in the dark phase, when rats consume most of their food. The body weight of each rat and its food and water intake are to be measured on every morning of the study; readings are to be taken in the final stage of the light phase at ~09:45 h. All diets are to be provided as a powder to control as far as possible for differences in physical form which may have affected diet preference.

During the training period, an extra food jar (along with the jar containing normal chow) containing chocolate are to be added to the cage for 2 hr/day intermittently, for at least three weeks, using the access schedule above. On the test day, rats are to be weighed in the final stage of the light phase and then dosed with pimavanserin or an appropriate vehicle. The chocolate and chow consumed during this 2 h period are to be measured. The body weights of the rats and the quantity of chow and water that the rats consumed in the 24 h after dosing (including consumption in the binge session) are also to be measured the following morning.

The doses of pimavanserins to be used are 0.1 mg/kg-10 mg/kg. When rats are administered pimavanserin (0.1, 0.5, 1.0, 3.0, 6.0, 10.0 mg/kg po) 60 min (or optionally 30 min or 120 min or 24 hours or some other time interval may be used) prior to a 2 h binge-eating session on chocolate, the pimavanserin shall decrease the consumption of this palatable food. The decrease is likely dose dependent and the doses shall have no effect on the consumption of standard laboratory diet during the 2 h binge-eating session compared to vehicle treated control.

The method described above may be used to show BED behavior in rats, and the usefulness of pimavanserin to treat BED.

Example of a pimavanserin study to functionally assess both measures of ICD and motor function As discussed above, therapies to treat ICDs that do not impair motor function nor interfere with DA replacement therapies are needed. To assess both measures of ICD and motor function, a protocol was developed that allows for concurrent testing of PD-like motor dysfunction (akinesia) and impulsivity related to ICDs observed in vulnerable dopamine agonist-treated PD patients.

Impulsiveness includes a greater tendency for risk-taking. This tendency can be quantified using probability discounting procedures; a cross-species assessment in which the subject chooses between a small reinforcer (SR) delivered at a high probability, and a large reinforcer (LR) delivered at a low probability. Typically, the subjective value of the LR is discounted when its probability is low, and individuals then select the smaller, yet more certain reinforcer. Those who suffer from ICD are less sensitive to low probabilities than healthy individuals, and they more frequently select the LR even when the odds to obtain the reward are very low (Hendrickson, et al., Effects of mindful eating training on delay and probability discounting for food and money in obese and healthy-weight individuals. Behav. Res. Ther. 51, 399-409, 2013).

Discounting tasks also have been implemented in a rat model of PD (rats with 6-hydroxydopamine (6OHDA)-induced lesions of the dorsolateral striatum (DLS)), using intracranial self-stimulation (ICSS) as positive reinforcers. Furthermore, administration of pramipexole (PPX), a D2 dopamine receptor agonist used to treat motor dysfunction in PD patients, increases ICSS-mediated probability discounting (Napier et al., Pramipexole-induced increased probabilistic discounting: comparison between a rodent model of Parkinson's disease and controls. Neuropsychopharmacology 37, 1397-1408, 2012).

Male Sprague-Dawley (outbred) rats (250-300 g; Harlan Laboratories, Indianapolis, Ind.) are to be pair-housed under environmentally controlled conditions under a 12 h light/dark cycle (lights on at 07:00); food and water are to be available ad libitum.

6-OHDA lesions will be carried out at described previously (Napier et al., Pramipexole-induced increased probabilistic discounting: comparison between a rodent model of Parkinson's disease and controls. Neuropsychopharmacology 37, 1397-1408, 2012). Prior to inducing lesions, desipramine (obtained from Sigma-Aldrich), a norepinephrine reuptake inhibitor, will be administered (25 mg/kg subcutaneously (sc)) to enhance selectivity of 6OHDA for dopamine neurons. Rats were anesthetized with isoflurane and secured in a stereotaxic frame. To create lesions, 6OHDA (7 µg or similar amount) will be bilaterally infused (0.2 µL/min for 10 min) into the dorsolateral striatum (DLS) at the following coordinates from Bregma: +1.0 mm AP, ±3.4 mm ML; −4.7 mm DV (optionally similar coordinates may be used) from skull. After the 6OHDA injection, a bipolar stimulating electrode (MS303/3-B/SPC; Plastics One, Roanoke, Va.) is to be lowered to the lateral hypothalamus (LH) for ICSS (from Bregma: −2.6 mm AP; −1.8 mm ML; −8.4 mm DV from skull), and the electrode plug held in place with dental acrylic affixed to stainless steel screws secured in the skull. At least one week recovery time will be allowed before initiating operant task training. ICSS does not occur if electrode tips are located outside the LH, however tip location within the LH does not correlate with ICSS-mediated outcomes (Floresco et al., Dopaminergic modulation of risk-based decision making. Neuropsychopharmacology 34, 681-697, 2009).

Rats then will be trained for ICSS followed by probability discounting. Once a stable baseline is obtained, rats will receive a subcutaneous osmotic minipump that released pramipexole at a rate of 0.3 mg/kg/day or 1.2 mg/kg/day (optionally similar dosages may be used). Pramipexole will be infused for 14 days (optionally a similar time period may be used), during which probability discounting will be assessed each day. Forelimb akinesia will be evaluated before lesion, after lesion, and at various time points during pramipexole administration. To assess the effects of pimavanserin and pramipexole on forelimb akinesia in the 6-OHDA lesioned rats, a forelimb step task will be used (Chang et al., Biochemical and anatomical characterization of forepaw adjusting steps in rat models of Parkinson's disease: studies on medial forebrain bundle and striatal lesions. Neuroscience 88, 617-628, 1999). To assess the effects of pimavanserin on pramipexole-induced risk-taking using parameters of the ICSS-mediated probability discounting task that were previously established (Napier et al., Intracranial self-stimulation as a positive reinforcer to study impulsivity in a probability discounting paradigm. J. Neurosci. Methods 198, 260-269, 2011), pramipexole (1.2 mg/kg/day (optionally a similar dose may be used) will be infused for a total of 28 days (optionally a similar length of time may be used). On day 14 (optionally another timing may be used) of pramipexole treatment, a second osmotic minipump will be implanted that releases pimavanserin at a dose rate of 0.1 or 0.3 or 1 or 3 or 6 or 10 mg/kg/day for 14 days (optionally a similar length of time may be used). Probability discounting will be assessed each day of chronic drug treatment; forelimb akinesia will be evaluated before lesion, after lesion, and at various time points during chronic drug administration.

Infusion of pramipexole (1.2 mg/kg/day or similar dose) for 14 days increased the risk taking behavior of rats as assessed by an increased proportion of selection of the LR delivered at a low probability, and it restored motor function as assessed by a reduction in forelimb akinesia. Co-administration of pimavanserin reduced risk taking behavior in rats receiving pramipexole as assessed by the proportion of rats selecting LR, but did not alter motor function in these animals.

Currently, there are no FDA-approved pharmacotherapies for ICDs with neurological comorbidities. These results showing A) suppression of pramipexole-induced risk taking by concommittant administration of pimavanserin as assessed by a reduction in the rate of responding to low probability, large reinforcers and B) lack of effect on restoration of motor function by pramipexole suggests pimavanserin may be useful in treating ICD in PD patients.

Example of Clinical Trial Design

The trial can be a multi-site, 8-week, randomized, double-blind, parallel, placebo-controlled, comparative, evaluating the efficacy of pimavanserin versus placebo. Suitably 40 mg of pimavanserin tartrate, containing 17 mg pimavanserin per tablet, is administered as 2×20 mg oral tablets once a day, for a total dose of 34 mg of pimavanserin per day. Identically designed placebo tablets are administered to the subjects in the placebo arm.

At least 100 subjects should be allowed into the study in order to have at least 50 subjects in each arm. The subjects should have been diagnosed with Parkinson's disease for at least one year and on stabile DRT or dopamine agonist treatment for at least three months. Additionally the subjects should have a QUIP-RS total score of at least 10, obtained from the sum of the sub-scores obtained from gambling, buying, eating, and hypersexuality.

QUIP-RS is to be used just before initiating the trial in order to set the baseline (W0), and thereafter half-way through the study (W4), and again at the end of the study (W8). In order to determine the severity of ICD the total score is to be evaluated compared to the score obtained at W0. Equally the scores from the individual sub-groups (gambling, buying, eating, and hypersexuality) are to be analyzed.

What is claimed:

1. A method for treating an impulse control disorder (ICD) in a patient comprising administering to the patient a compound of Formula (I) or a pharmaceutically acceptable salt thereof:

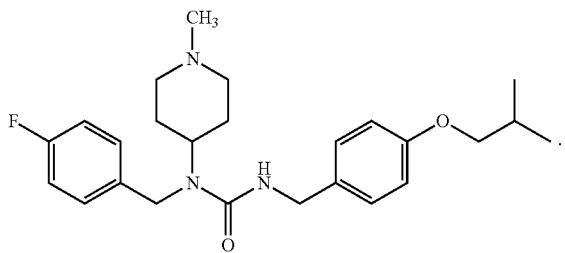

(I)

2. The method of claim 1, wherein the impulse control disorder treated is an impulse selected from the group consisting of hypersexuality, gambling, buying, eating, punding, hobbyism, walkabout, hoarding, dopamine dysregulation syndrome and addiction.

3. The method of claim 1, wherein the impulse treated is selected from the group consisting of hypersexuality, gambling, buying, and eating.

4. The method of claim 3, wherein the hypersexuality is compulsive sexual behaviour, the gambling is pathological gambling, the buying is compulsive buying and eating is binge-eating disorder.

5. The method of claim 1, wherein the compound according to Formula (I) or a pharmaceutically acceptable salt thereof decreases 5HT2A receptor activity.

6. The method of claim 1, wherein the patient has been diagnosed with Parkinson's disease.

7. The method of claim 1, wherein the patient is on dopamine replacement therapy (DRT) or has been administered a dopamine agonist.

8. The method of claim 7, wherein the patient has been subject to a change in the dopamine replacement therapy (DRT) or has been subject to a change in the administration of the dopamine agonist.

9. The method of claim 8, wherein the change is a dose adjustment.

10. The method of claim 8, wherein the change is an increased dose.

11. The method of claim 1, wherein the patient is administered levodopa.

12. The method of claim 1, wherein the patient is administered a dopamine agonist.

13. The method of claim 1, wherein the patient fulfils one or more of the following: a personal or familial history of alcoholism or gambling; impulsive or novelty seeking traits; male sex; early onset of PD; being unmarried; and past or current cigarette smoking.

14. The method of claim 1, wherein the ICD severity is evaluated using the total ICD score using Questionnaire for Impulsive-Compulsive Disorders in Parkinson's Disease-Rating Scale (QUIP-RS).

15. The method of claim 1, wherein the ICD severity in the patient is evaluated after being administered compound of Formula (I) or a pharmaceutically acceptable salt thereof for at least 8 weeks.

16. The method of 1, wherein the ICD severity in the patient is evaluated after being administered a compound of Formula (I) or a pharmaceutically acceptable salt thereof for at least 4 weeks.

17. The method of claim 14, wherein the total ICI) score using QUIP-RS is at least −10 points after the patient being administered a compound of Formula (I) or a pharmaceutically acceptable salt thereof for at least 4 weeks compared to prior to the administration.

18. The method of claim 1, wherein an effective amount of the compound of Formula (I) or a pharmaceutically acceptable salt thereof is administered to the patient.

19. The method according to claim 18, wherein the effective amount of the compound of Formula (I) is a dose selected from the group consisting of 8.5 mg, 12.75 mg, 17 mg, 21.25 mg, 25.5 mg, 29.75 mg, and 34 mg of the compound of Formula (I).

20. The method of claim 14, wherein the total ICD score using QUIP-RS is at least −10 points after the patient being administered a compound of Formula (I) or a pharmaceutically acceptable salt thereof for 8 weeks.

* * * * *